(12) United States Patent
Siegel

(10) Patent No.: US 10,080,657 B2
(45) Date of Patent: Sep. 25, 2018

(54) CATHETER BASED APICAL APPROACH HEART PROSTHESES DELIVERY SYSTEM

(71) Applicant: CEDARS-SINAI MEDICAL CENTER, Los Angeles, CA (US)

(72) Inventor: Robert James Siegel, Beverly Hills, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 80 days.

(21) Appl. No.: 14/771,704

(22) PCT Filed: Mar. 5, 2014

(86) PCT No.: PCT/US2014/020867
§ 371 (c)(1),
(2) Date: Aug. 31, 2015

(87) PCT Pub. No.: WO2014/138284
PCT Pub. Date: Sep. 12, 2014

(65) Prior Publication Data
US 2016/0000562 A1 Jan. 7, 2016

Related U.S. Application Data

(60) Provisional application No. 61/774,513, filed on Mar. 7, 2013.

(51) Int. Cl.
*A61F 2/24* (2006.01)
(52) U.S. Cl.
CPC .......... *A61F 2/2427* (2013.01); *A61F 2/2466* (2013.01)
(58) Field of Classification Search
CPC ............................. A61F 2/2427; A61F 2/2466
See application file for complete search history.

(56) References Cited

U.S. PATENT DOCUMENTS 4,777,951 A 10/1988 Cribier et al.
5,201,880 A 4/1993 Wright et al.
(Continued)

FOREIGN PATENT DOCUMENTS

EP 1 674 040 6/2006
EP 1 539 015 4/2011
(Continued)

OTHER PUBLICATIONS

International Preliminary Report on Patentability issued in PCT Application No. PCT/US2014/020867, dated Sep. 8, 2015, in 11 pages.
(Continued)

*Primary Examiner* — Ashley Fishback
(74) *Attorney, Agent, or Firm* — Knobbe Martens Olson & Bear LLP

(57) ABSTRACT

A delivery system for rapid placement of heart implants is provided that includes a delivery platform. The delivery system includes a tubular catheter body, a piercing member, and a delivery platform. The tubular catheter body is sufficiently long and flexible to be advanced from a peripheral blood vessel access site to an atrium of the heart. The piercing member is configured to create a transapical channel from an internal apical portion of a ventricle to an outside heart wall. The delivery system includes an elongate tension member and an enlargeable member disposed on a distal portion of the elongate tension member. The enlargeable member is configured to be enlarged in a pericardial space of an intact chest wall to cover an area of the outside heart wall surrounding an opening of the transapical channel. When tensioned, the tension member provides a stable zone for positioning a heart implant within the heart.

20 Claims, 16 Drawing Sheets

(56) References Cited

U.S. PATENT DOCUMENTS

| | | |
|---|---|---|
| 5,573,540 A | 11/1996 | Yoon |
| 5,575,799 A | 11/1996 | Bolanos et al. |
| 5,609,598 A | 3/1997 | Laufer et al. |
| 5,626,588 A | 5/1997 | Sauer et al. |
| 5,716,367 A | 2/1998 | Koike et al. |
| 6,029,671 A | 2/2000 | Stevens et al. |
| 6,051,014 A | 4/2000 | Jang |
| 6,090,096 A | 7/2000 | St. Goar et al. |
| 6,117,144 A | 9/2000 | Nobles et al. |
| 6,117,145 A | 9/2000 | Wood et al. |
| 6,136,010 A | 10/2000 | Modesitt et al. |
| 6,165,183 A | 12/2000 | Kuehn et al. |
| 6,197,043 B1 | 3/2001 | Davidson |
| 6,206,893 B1 | 3/2001 | Klein et al. |
| 6,269,819 B1 | 8/2001 | Oz et al. |
| 6,287,321 B1 | 9/2001 | Jang |
| 6,312,446 B1 | 11/2001 | Huebsch et al. |
| 6,312,447 B1 | 11/2001 | Grimes |
| 6,325,067 B1 | 12/2001 | Sterman et al. |
| 6,328,757 B1 | 12/2001 | Matheny |
| 6,461,366 B1 | 10/2002 | Seguin |
| 6,575,971 B2 | 6/2003 | Hauck et al. |
| 6,629,534 B1 | 10/2003 | St. Goar et al. |
| 6,635,068 B1 | 10/2003 | Dubrul et al. |
| 6,752,813 B2 | 6/2004 | Goldfarb et al. |
| 6,770,083 B2 | 8/2004 | Seguin |
| 6,926,715 B1 | 8/2005 | Hauck et al. |
| 6,932,792 B1 | 8/2005 | St. Goar et al. |
| 6,945,978 B1 | 9/2005 | Hyde |
| 7,048,754 B2 | 5/2006 | Martin et al. |
| 7,226,467 B2 | 6/2007 | Lucatero et al. |
| 7,563,267 B2 | 7/2009 | Goldfarb et al. |
| 7,569,062 B1 | 8/2009 | Kuehn et al. |
| 7,604,646 B2 | 10/2009 | Goldfarb et al. |
| 7,632,308 B2 | 12/2009 | Loulmet |
| 7,635,329 B2 | 12/2009 | Goldfarb et al. |
| 7,666,204 B2 | 2/2010 | Thornton et al. |
| 7,704,269 B2 | 4/2010 | St. Goar et al. |
| 7,736,388 B2 | 6/2010 | Goldfarb et al. |
| 7,811,296 B2 | 10/2010 | Goldfarb et al. |
| 7,828,819 B2 | 11/2010 | Webler et al. |
| 7,854,762 B2 | 12/2010 | Speziali et al. |
| 7,938,827 B2 | 5/2011 | Hauck et al. |
| 7,981,123 B2 | 7/2011 | Seguin |
| 8,123,703 B2 | 2/2012 | Martin et al. |
| 8,172,856 B2 | 5/2012 | Eigler et al. |
| 8,216,256 B2 | 7/2012 | Raschdorf, Jr. et al. |
| 8,216,302 B2 | 7/2012 | Wilson et al. |
| 8,303,608 B2 | 11/2012 | Goldfarb et al. |
| 8,323,334 B2 | 12/2012 | Deem et al. |
| 8,409,273 B2 | 4/2013 | Thornton et al. |
| 8,545,551 B2 | 10/2013 | Loulmet |
| 8,568,472 B2 | 10/2013 | Marchand et al. |
| 8,992,605 B2 | 3/2015 | Zakai et al. |
| 9,023,099 B2 | 5/2015 | Duffy et al. |
| 9,060,858 B2 | 6/2015 | Thornton et al. |
| 9,474,605 B2 | 10/2016 | Rowe et al. |
| 9,498,330 B2 | 11/2016 | Solem |
| 9,763,658 B2 | 9/2017 | Eigler et al. |
| 2001/0005787 A1 | 6/2001 | Oz et al. |
| 2002/0013571 A1 | 1/2002 | Goldfarb et al. |
| 2003/0120340 A1 | 6/2003 | Liska et al. |
| 2004/0044350 A1 | 3/2004 | Martin et al. |
| 2004/0260322 A1 | 12/2004 | Rudko et al. |
| 2005/0033446 A1 | 2/2005 | Deem et al. |
| 2005/0107871 A1 | 5/2005 | Realyvasquez et al. |
| 2005/0143811 A1 | 6/2005 | Realyvasquez |
| 2005/0222489 A1 | 10/2005 | Rahdert et al. |
| 2006/0229708 A1 | 10/2006 | Powell et al. |
| 2006/0293739 A1 | 12/2006 | Vijay |
| 2007/0032850 A1 | 2/2007 | Ruiz et al. |
| 2007/0038293 A1 | 2/2007 | St.Goar et al. |
| 2007/0055303 A1 | 3/2007 | Vidlund et al. |
| 2007/0270943 A1 | 11/2007 | Solem et al. |
| 2009/0048668 A1 | 2/2009 | Wilson et al. |
| 2009/0177266 A1 | 7/2009 | Powell et al. |
| 2010/0217283 A1 | 8/2010 | St.Goar et al. |
| 2010/0298929 A1 | 11/2010 | Thornton et al. |
| 2011/0029071 A1 | 2/2011 | Zlotnick et al. |
| 2011/0066233 A1 | 3/2011 | Thornton et al. |
| 2011/0106245 A1 | 5/2011 | Miller et al. |
| 2011/0218620 A1 | 9/2011 | Meiri et al. |
| 2011/0224655 A1 | 9/2011 | Asirvatham et al. |
| 2011/0264208 A1 | 10/2011 | Duffy et al. |
| 2011/0319989 A1 | 12/2011 | Lane et al. |
| 2012/0010700 A1 | 1/2012 | Spenser |
| 2012/0065464 A1 | 3/2012 | Ellis et al. |
| 2012/0078360 A1 | 3/2012 | Rafiee |
| 2012/0095547 A1 | 4/2012 | Chuter |
| 2012/0116418 A1 | 5/2012 | Belson et al. |
| 2012/0191181 A1 | 7/2012 | Kassab et al. |
| 2012/0245678 A1 | 9/2012 | Solem |
| 2012/0310331 A1 | 12/2012 | Eigler et al. |
| 2012/0310334 A1 | 12/2012 | Dolan |
| 2013/0018414 A1 | 1/2013 | Widimski et al. |
| 2013/0030522 A1 | 1/2013 | Rowe et al. |
| 2013/0253547 A1 | 9/2013 | Goldfarb et al. |
| 2014/0039607 A1 | 2/2014 | Kovach |
| 2014/0058502 A1 | 2/2014 | Marchand et al. |
| 2014/0236198 A1 | 8/2014 | Goldfarb et al. |
| 2016/0008129 A1 | 1/2016 | Siegel |
| 2017/0143478 A1 | 5/2017 | Schwartz et al. |
| 2017/0245988 A1 | 8/2017 | Siegel et al. |

FOREIGN PATENT DOCUMENTS

| | | |
|---|---|---|
| WO | WO 00/60995 | 10/2000 |
| WO | WO 01/26557 | 4/2001 |
| WO | WO 03/049619 | 6/2003 |
| WO | WO 2004/012583 | 2/2004 |
| WO | WO 2014/138482 | 9/2014 |
| WO | WO 2016/040526 | 3/2016 |
| WO | WO 2016/077783 | 5/2016 |
| WO | WO 2017/015632 | 1/2017 |

OTHER PUBLICATIONS

Bhargava et al., "Biosense Left Ventricular Electromechanical Mapping", Asian Cardiovasc Thorac Ann 1999, 7:345-52.

Black MD, M., Divisiona of Pediatric Cardiac Surgery, Standford University School of Medicine, California, USA, Minimally Invasive Pediatric Cardiac Surgery, Online Article in 4 pages.

Ethicon Wound Closure Manual—Chapter 6, Research and Development at Ethicon, Inc—An Ongoing Process of Change and Improvement, Online at www.ethiconinc.com in 4 pages.

Gersak MD, Ph.D., B., "Mitral Valve Repair or Replacement on the Beating Heart", The Heart Surgery Forum #2000-1989, Jun. 8, 2000, pp. 232-237, 2000 Forum Multimedia Publishing, LLC.

Perclose A-T, 6F Suture-Mediated Closure (SMC) System, Instructions for Use disctributed in the U.S. by Abbott laboratories, Inc. 2002, 2006 Abbott Laboratories in 11 pages.

Quealy et al., "Use of Combined Intravascular Ultrasound and PTCA Catheter: Clinical Utility", Chapter 12, pp. 245-250.

International Search Report and Written Opinion issued in PCT Application No. PCT/US2014/020867, dated Jun. 23, 2014, in 22 pages.

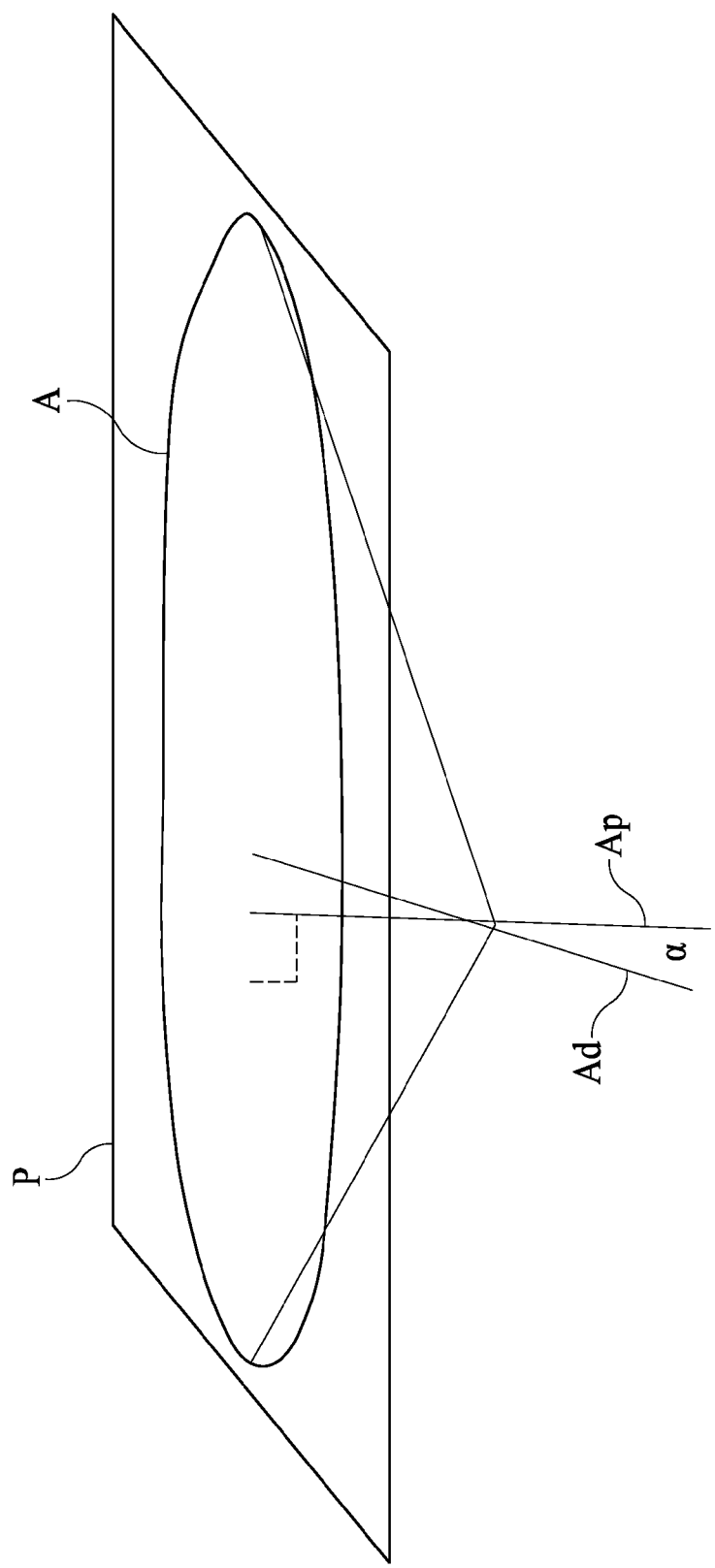

CATHETER BASED APICAL APPROACH HEART PROSTHESES DELIVERY SYSTEM

BACKGROUND OF THE INVENTION

Field of the Invention

This application is directed to systems and methods for implanting devices in human hearts from a catheter approach.

Description of the Related Art

Catheters are in widespread use for a wide number of procedures. In recent years, complex devices such as aortic valves have been delivered using catheters. These catheter based procedures provide benefits for patients, including reduced trauma compared to surgical techniques for accomplishing similar outcomes, e.g., aortic valve replacement.

Limitations of catheter based techniques have spurred efforts to develop a less invasive surgical technique that can be performed through cannulae inserted into the heart through the chest wall. These procedures have advantages, such as moving the proximal end of the tools used to perform the procedure closer to the surgical site.

Various downsides remain, however. For one, access to the heart through the chest wall is more complex than access to a superficial peripheral vessel, such as a femoral artery. For example, a surgical window must still be opened to advance the surgical cannulae through the skin and intervening tissue to the heart. The outside surface of the heart is a convex and tough structure that may not be easy to pierce from the outside surface. Thus, the chest wall access site may need to be enlarged, taking away the benefits of small cannulae.

SUMMARY OF THE INVENTION

Among the realizations described herein is the notion that catheter-based heart procedures can be greatly expanded by providing a delivery system that can be advanced from superficial peripheral vessels to the heart and through the heart wall to provide a taut delivery platform (sometimes called a "rail" herein) over which to deliver tools for preparing an implant site and a variety of implants.

In one embodiment, a method of placing a cardiac device in a heart of a patient is provided. Vascular access is provided at a peripheral superficial venous blood vessel. An access catheter is advanced through the peripheral superficial venous blood vessel, through the vena cava into the heart. A distal portion of the access catheter is advanced across the intra-atrial septum into the left atrium. A proximal portion of a delivery platform is advanced out of the access catheter to a position superior of the mitral valve opening. A distal portion of the delivery platform is advanced into the left ventricle and through the heart wall. A procedure zone of the delivery platform between the distal portion and the proximal portion is tensioned. The procedure zone extends at least from superior to the mitral valve to inferior of the mitral valve.

In another embodiment a method of placing a cardiac device in a heart of a patient is provided. The method includes advancing a delivery system percutaneously from a peripheral blood vessel access site into a heart. The delivery system has an elongate member with an enlargeable device disposed at a distal portion thereof. The enlargeable device is anchored to a heart wall. The elongate member is tensioned. A procedure is performed along the elongate member. The elongate member is retracted proximally and out of the peripheral blood vessel access site.

In another embodiment, a delivery system for rapid placement of heart implants at a mitral valve is provided. The system includes a delivery platform and a heart valve implant catheter. The delivery system includes a tubular catheter body, a piercing member, and a delivery platform. The tubular catheter body is sufficiently long and flexible to be advanced from a peripheral blood vessel access site to an atrium of the heart. The piercing member is configured to be advanced from the tubular body to create a transapical channel from an internal apical portion of a ventricle to an outside heart wall. The delivery system includes an elongate tension member and an anchor member disposed on a distal portion of the elongate tension member. The enlargeable member is configured to be enlarged in a pericardial space of an intact chest wall to cover an area of the outside heart wall surrounding an opening of the transapical channel. At least the heart valve implant is separable from the delivery system such that the tension member and anchor can be removed while leaving the heart valve implant in place in the heart.

A delivery system for rapid placement of heart implants is provided that includes a delivery platform. The delivery system includes a tubular catheter body, a piercing member, and a delivery platform. The tubular catheter body is sufficiently long and flexible to be advanced from a peripheral blood vessel access site to an atrium of the heart. The piercing member is configured to create a transapical channel from an internal apical portion of a ventricle to an outside heart wall. The delivery system includes an elongate tension member and an enlargeable member disposed on a distal portion of the elongate tension member. The enlargeable member is configured to be enlarged in a pericardial space of an intact chest wall to cover an area of the outside heart wall surrounding an opening of the transapical channel. When tensioned, the tension member provides a stable zone for positioning a heart implant within the heart.

BRIEF DESCRIPTION OF THE DRAWINGS

A more complete appreciation of the subject matter of this application and the various advantages thereof can be realized by reference to the following detailed description, in which reference is made to the accompanying drawings in which:

FIG. 3A-1 is a cross-section similar to that of FIG. 3 showing another embodiment configured to be steerable;

More detailed descriptions of various embodiments of catheter based transapical delivery systems, components and methods useful to treat patients are set forth below.

DETAILED DESCRIPTION OF THE PREFERRED EMBODIMENT

Figure 1:
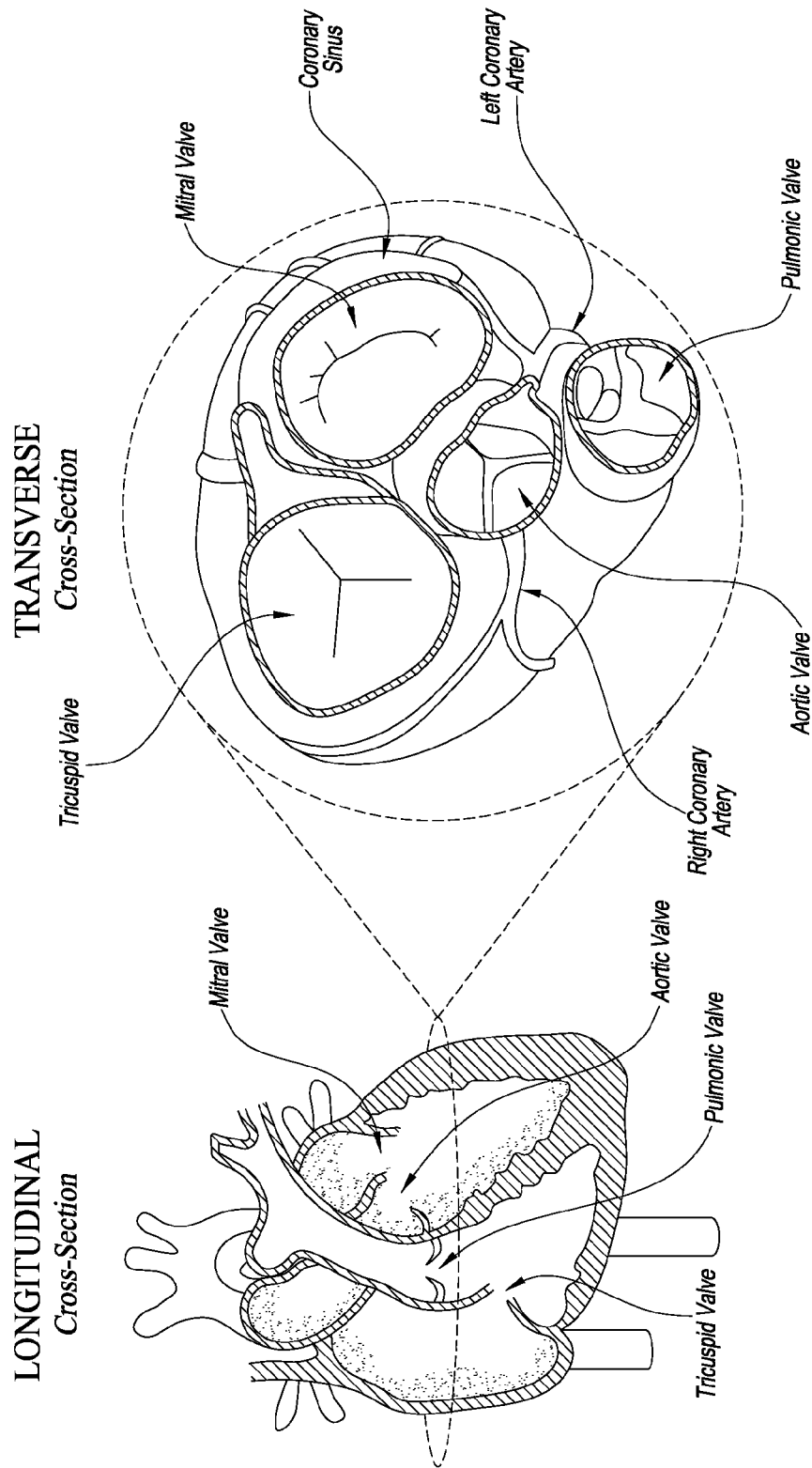
FIG. 1 is a schematic cross-sectional view of a human heart, showing some of the structures that can be accessed for procedures in accordance with embodiments discussed herein.

FIG. 1 is a cross-section of the heart showing its primary anatomy. In particular, the heart is divided into four major chambers, i.e., right atrium RA, left atrium LA, right ventricle RV and left ventricle LV. The mitral valve MV separates the LA and LV. The leaflets of the mitral valve are connected to heart walls and actuated by chordae tendonae. The tricuspid valve TV separates the RA from the RV. Blood is pumped out of the heart into the systemic circulation through the aortic valve AV and to the pulmonary vasculature through the pulmonic valve PV. The aorta extends from the AV over the aortic arch and branches to smaller arteries serving major organs. The pulmonary artery extends from the PV to the lungs where blood is oxygenated. The vena cava gather venous blood from the systemic circulation and returns it to the RA.

Figure 2:
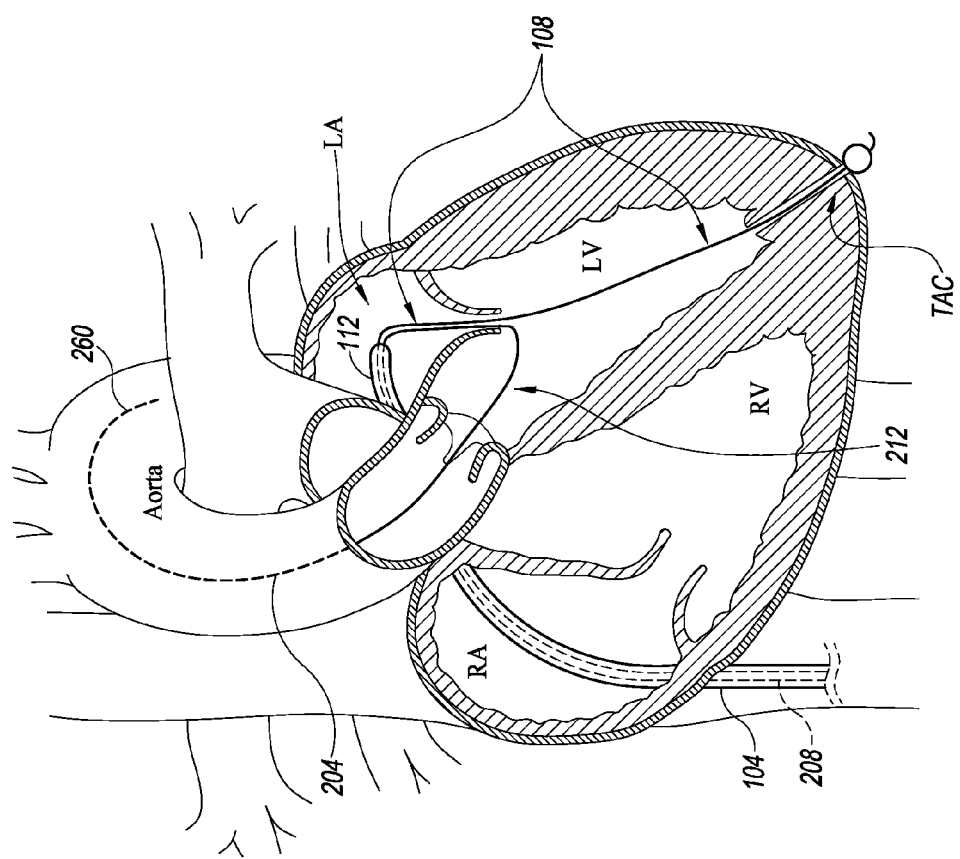
FIG. 2 is another schematic view of the heart showing an embodiment of a delivery system applied thereto.
Figure 3:
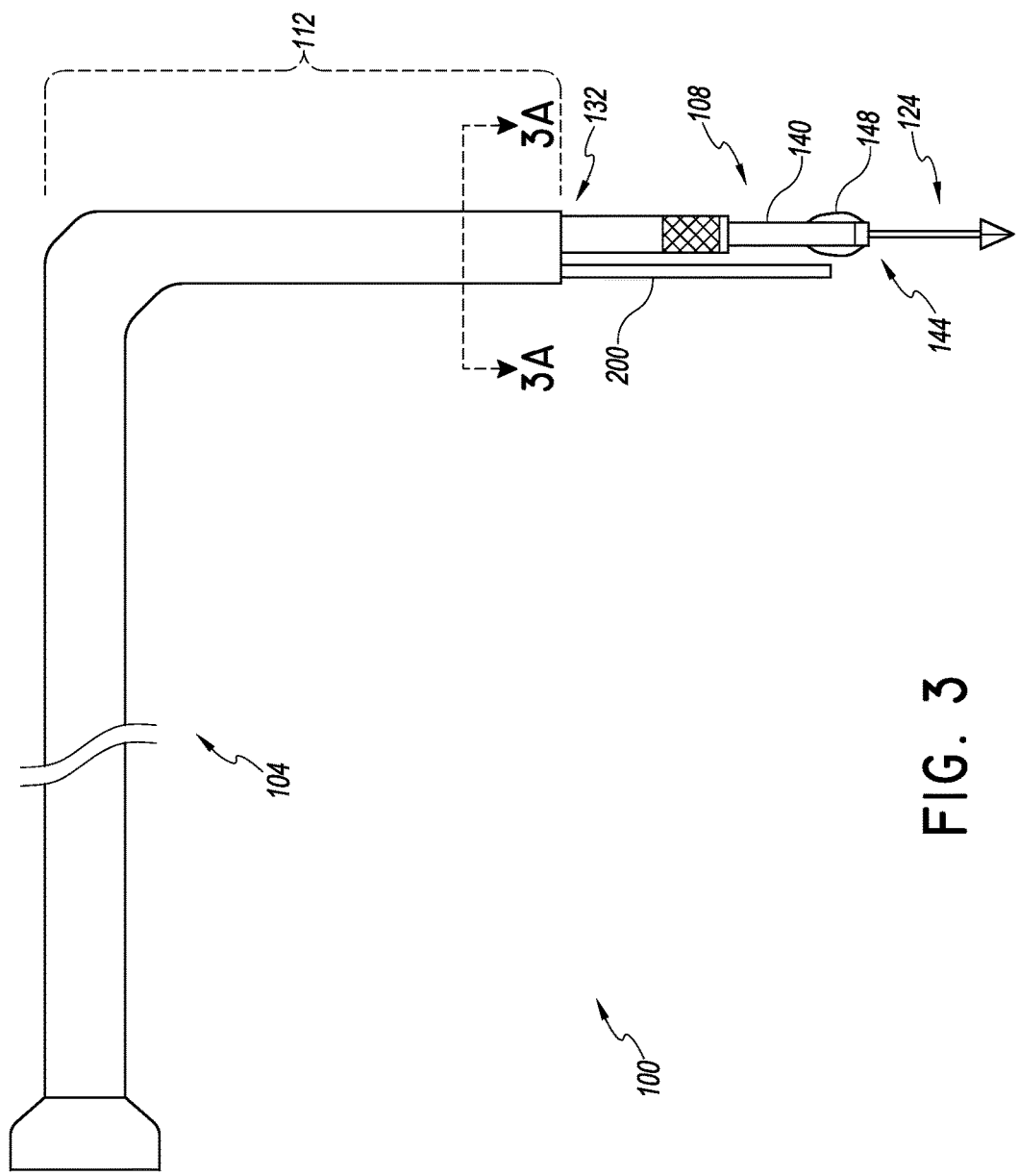
FIG. 3 is a plan view of delivery and preparation system that can be used as shown in FIG. 2.

As discussed above, various maladies affect these and other major structures of the heart. FIGS. 2 and 3 show a procedure and delivery system 100 and its placement in heart. In one embodiment, the system 100 is configured to deliver a mitral valve implant to the heart. The system 100 includes a tubular catheter body 104 and a delivery platform 108. The delivery platform 108 is configured to be tensioned to provide a predictable, stable structure for advancing and positioning devices in the mitral valve space and elsewhere in the heart.

The catheter body 104 can be configured in any way suitable to be advanceable from a peripheral blood vessel to the right atrium of the heart. One way to reach the left atrium is to access a femoral vein or other peripheral blood vessel. The catheter body 104 can be advanced from the femoral vein to the vena cava, through the eustacian valve into the right atrium. The access path from the venous vasculature is relatively straight. The catheter body 104 can be formed with a rigid polymer such as polyethylene and it may be optionally reinforced by a braided structure so that it is fairly rigid to a bending force (discussed below).

Preferably a distal portion 112 of the catheter body 104 is configured to traverse a lateral path through the right atrium to the intra-atrial septum. The lateral path is generally transverse to the path that the catheter body 104 traverses to approach the eustacian valve from the inferior venous vasculature. The lateral path can be facilitated by pre-shaping the catheter body 104 so that the catheter body 104 has an L shape when the catheter body is unconstrained. The lateral path can extend transverse to the right atrium to the fossa ovalis. In one embodiment the distal end of the distal portion 112 is sufficiently rigid to proceed through the fossa ovalis in response to gentle advancement by the clinician of a proximal portion of the catheter body 104. In another embodiment, the system 100 includes an access sheath (not shown) and the catheter body 104 is advanced through the sheath into the left atrium. The access sheath may be positioned across the atrial septum prior to delivery of the distal portion 112 across the intra-atrial septum via the fossa ovalis.

In the illustrated embodiment, the delivery platform 108 includes an elongate slender catheter body that can be disposed through the native mitral valve space and downward to the left ventricular apex.

Figure 4:
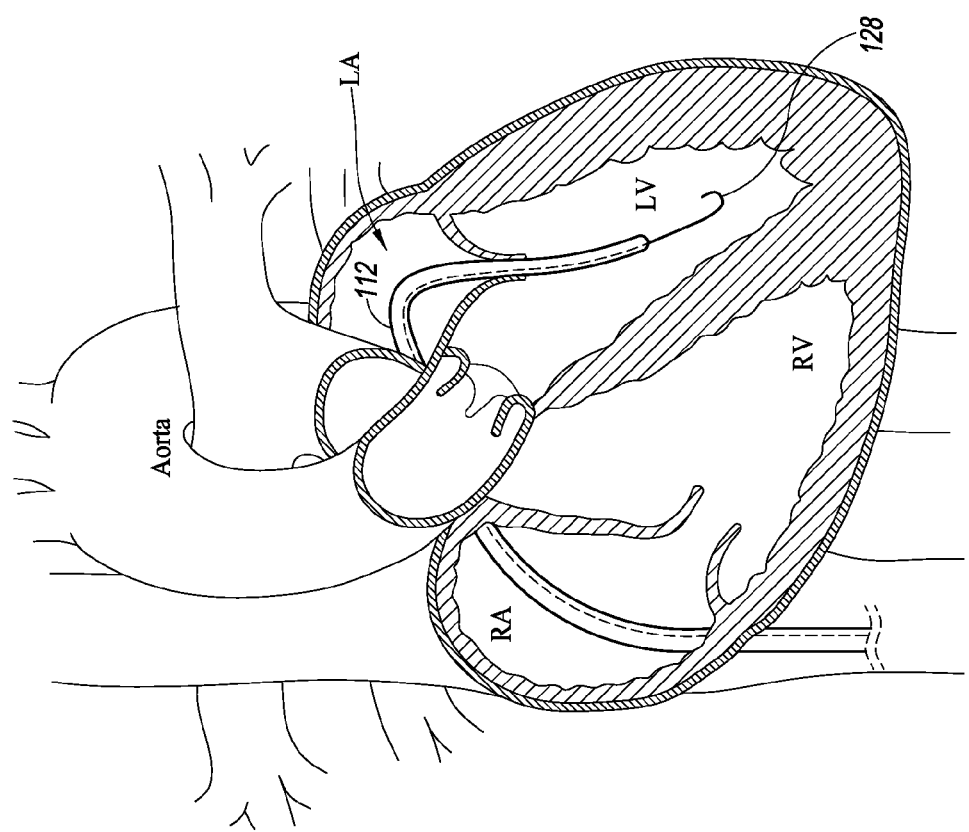
FIGS. 4-9 are schematic diagrams of various stages of various embodiments of methods of using the systems of FIGS. 3-3D and modified embodiments thereof.
Figure 5:
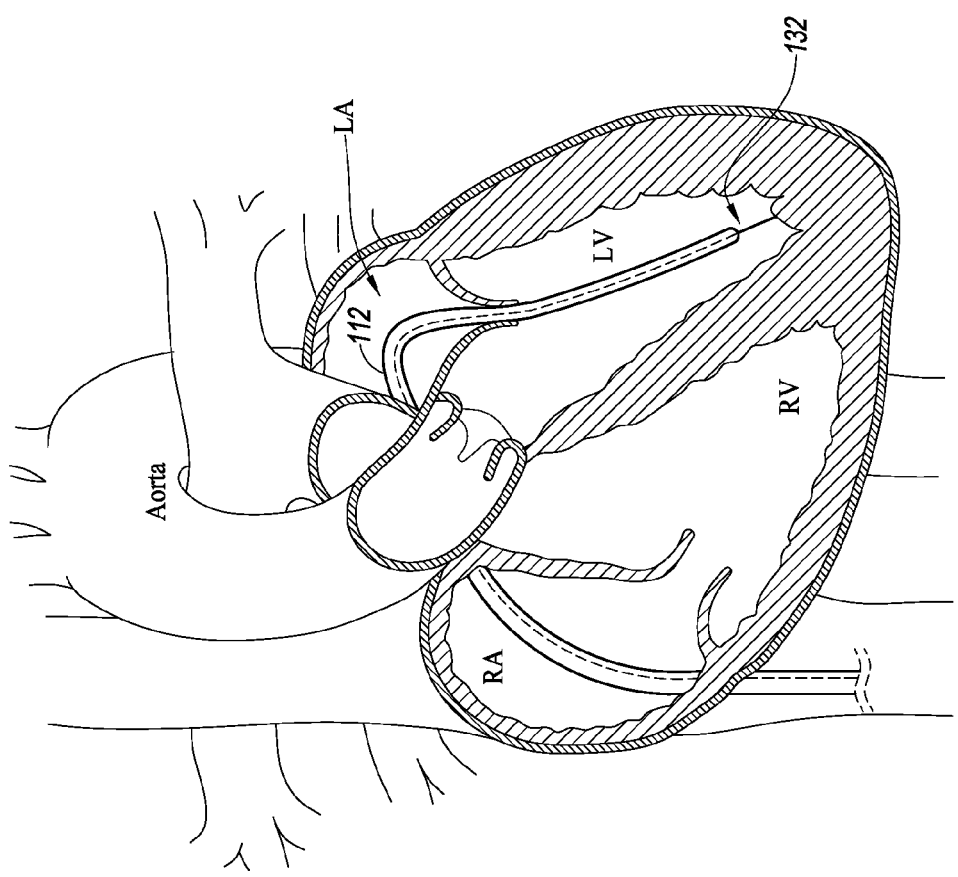
Figure 6:
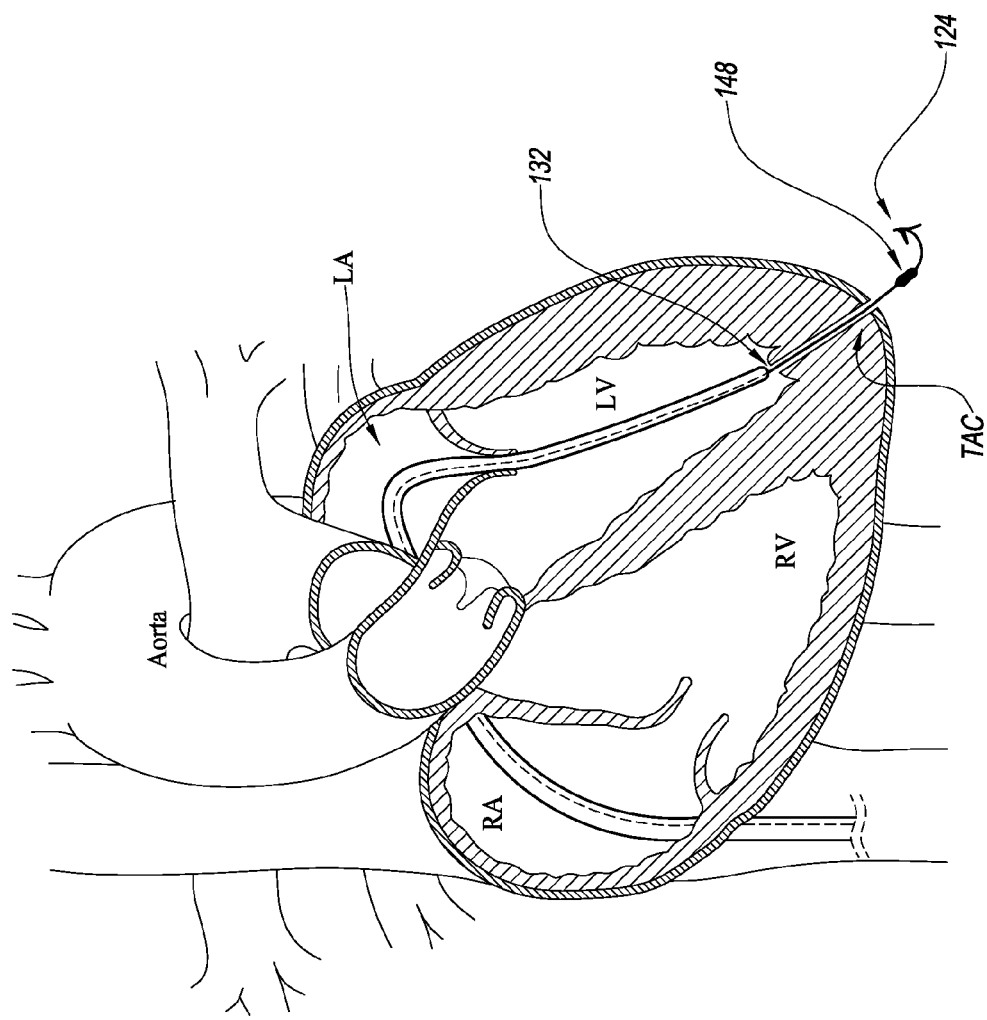

Preferably a piercing member 124 is provided in the delivery system 100 that facilitates placement of the delivery platform 112. FIG. 3B show the piercing member 124 disposed at the distal end of the elongate body 124A. The elongate body 124A can be solid as illustrated in FIG. 3B or hollow as in FIG. 3A. FIGS. 4-6 show one technique for using the piercing member 124 to place the delivery platform 112. In particular, a standard atraumatic tip guidewire 128 is advanced into the left ventricle. The catheter body 104 can be tracked over the guidewire into close proximity to the ventricular apex. FIG. 5 shows that the catheter body 104 can be advanced up to and in some cases in contact with the wall of the left ventricle at the apex. Thereafter, the piercing member 124 can be advanced out of a distal port 132 of the catheter body 104.

Figure 3A:
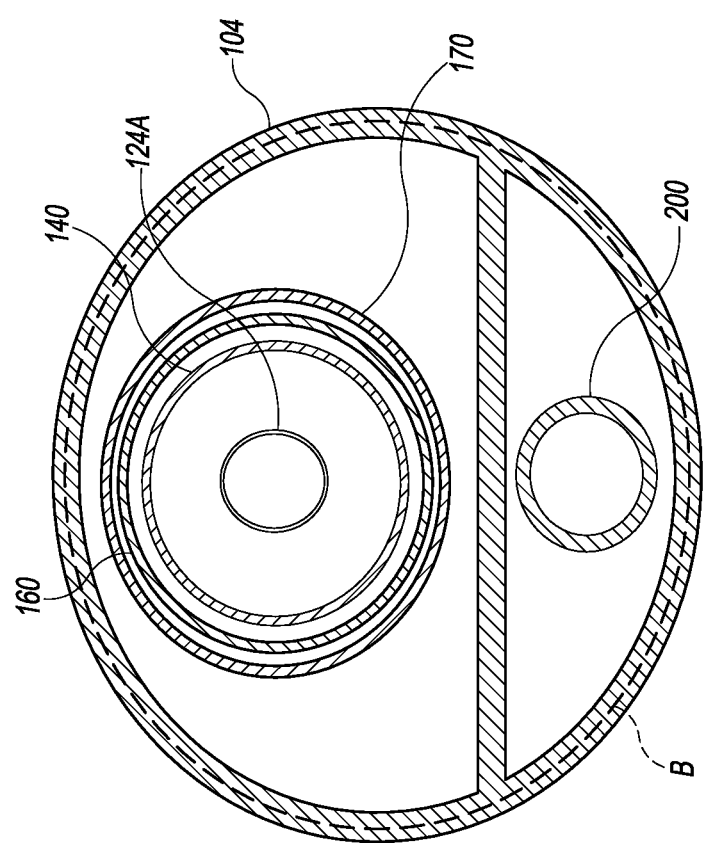
FIG. 3A is a cross-sectional view of the system of FIG. 3 taken at the plane 3A-3A.
Figures 1, 3A:
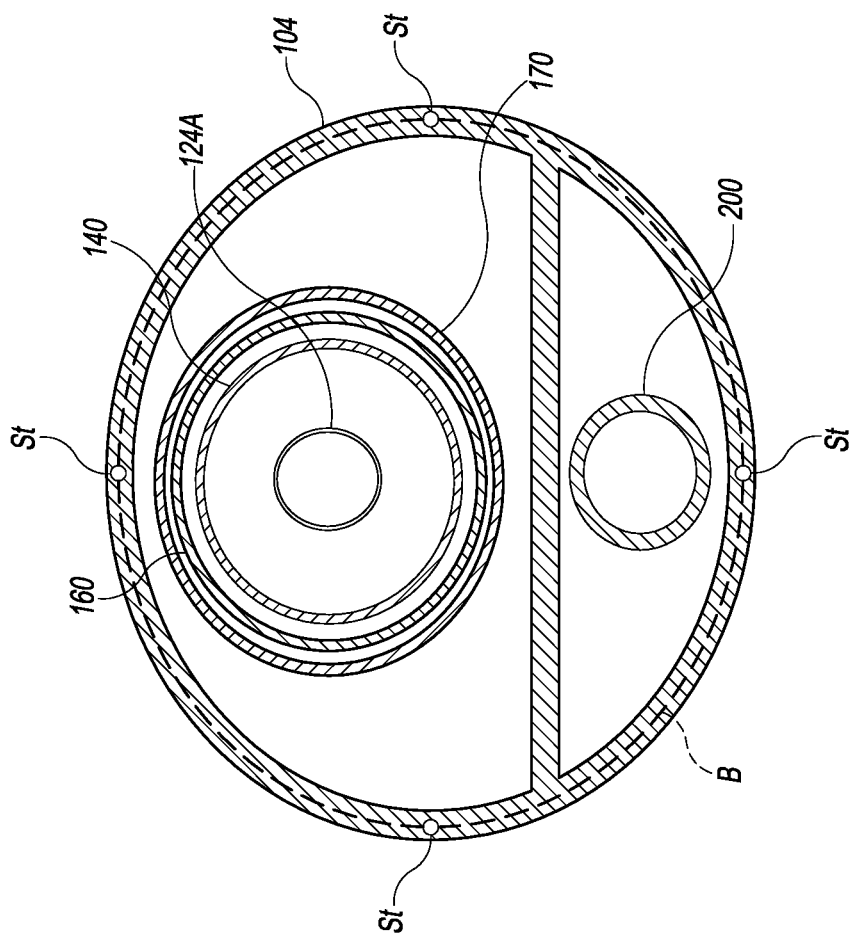
Figure 3B:
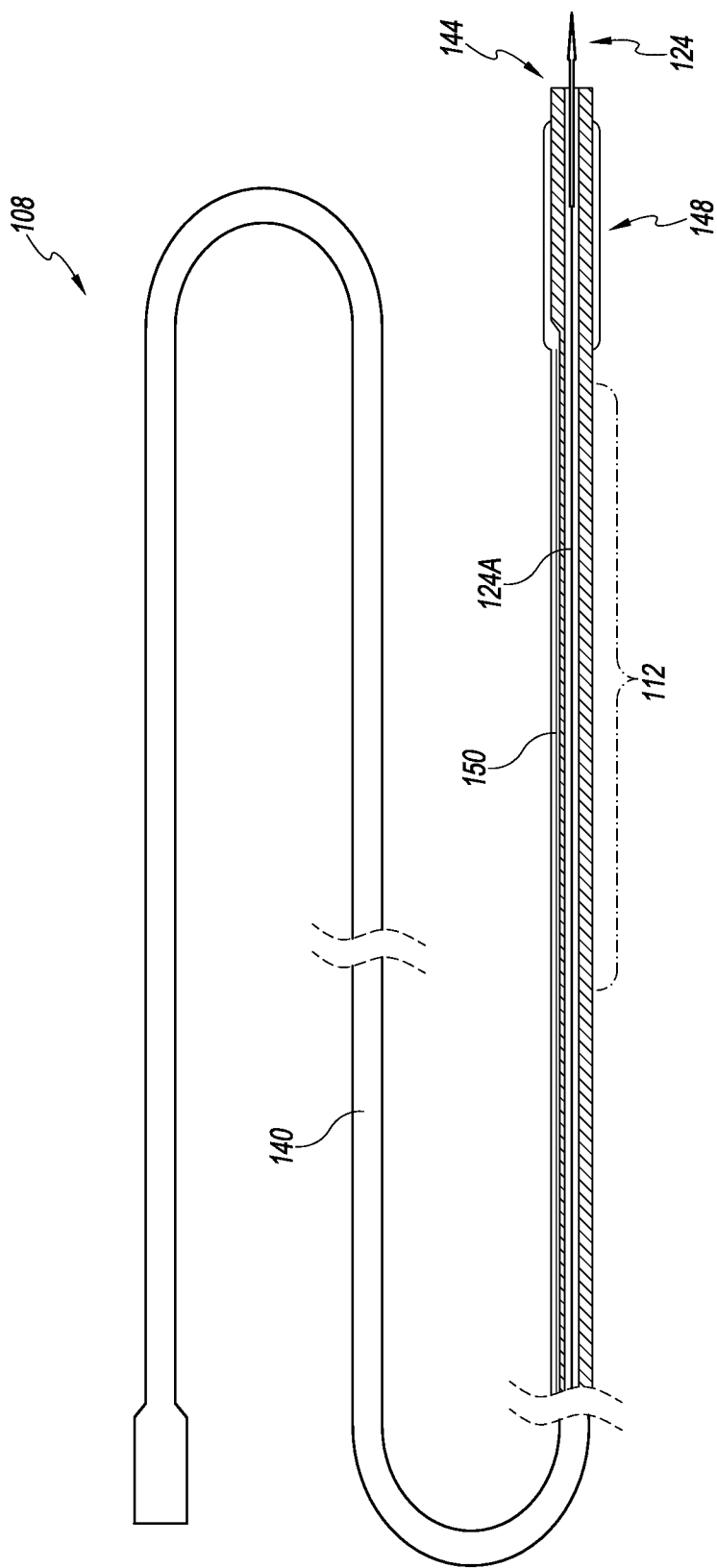
FIG. 3B is a plan view of a catheter having a delivery platform in which the distal section is in cross-section and is drawn to a larger scale than the proximal section to emphasize certain details.
Figure 3C:
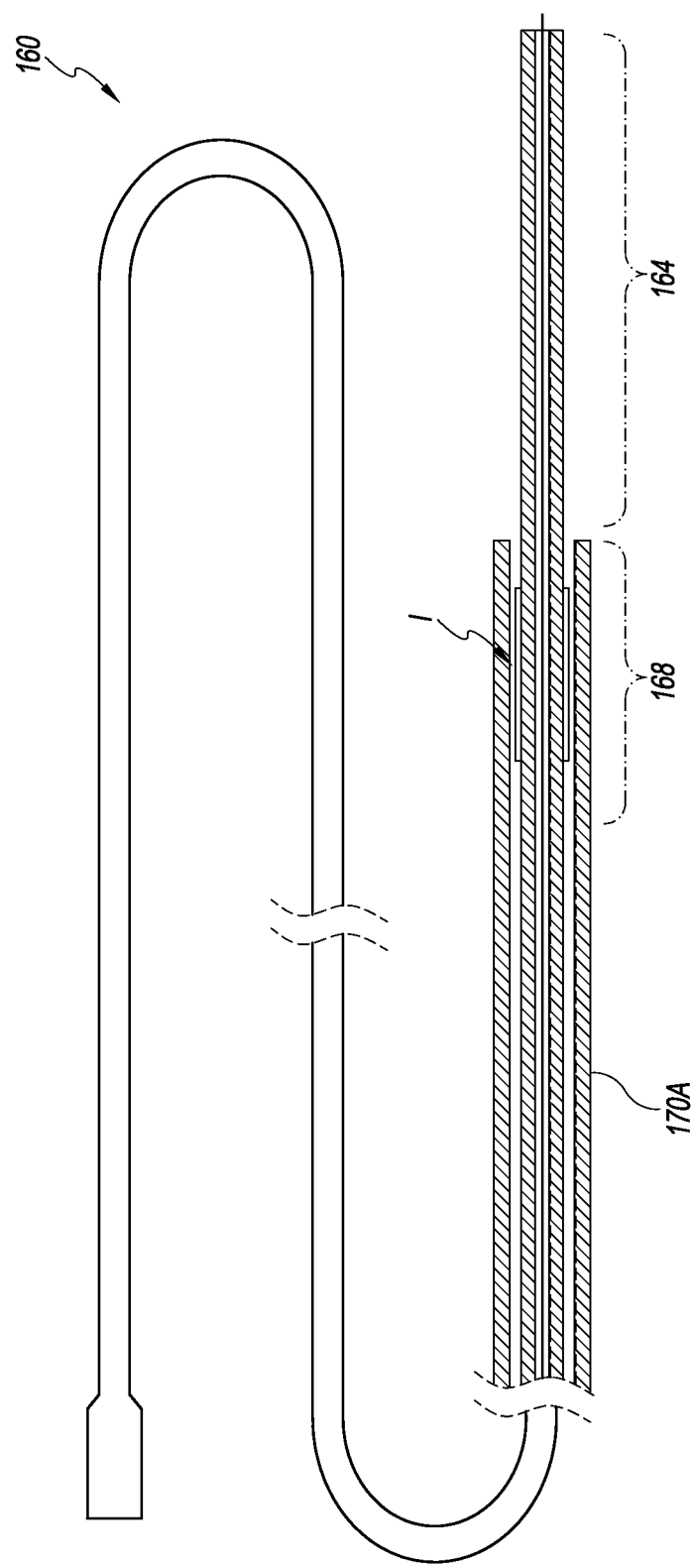
FIG. 3C is a plan view of an implant catheter in which the distal section is in cross-section and is drawn to a larger scale than the proximal section to emphasize certain details.
Figure 3D:
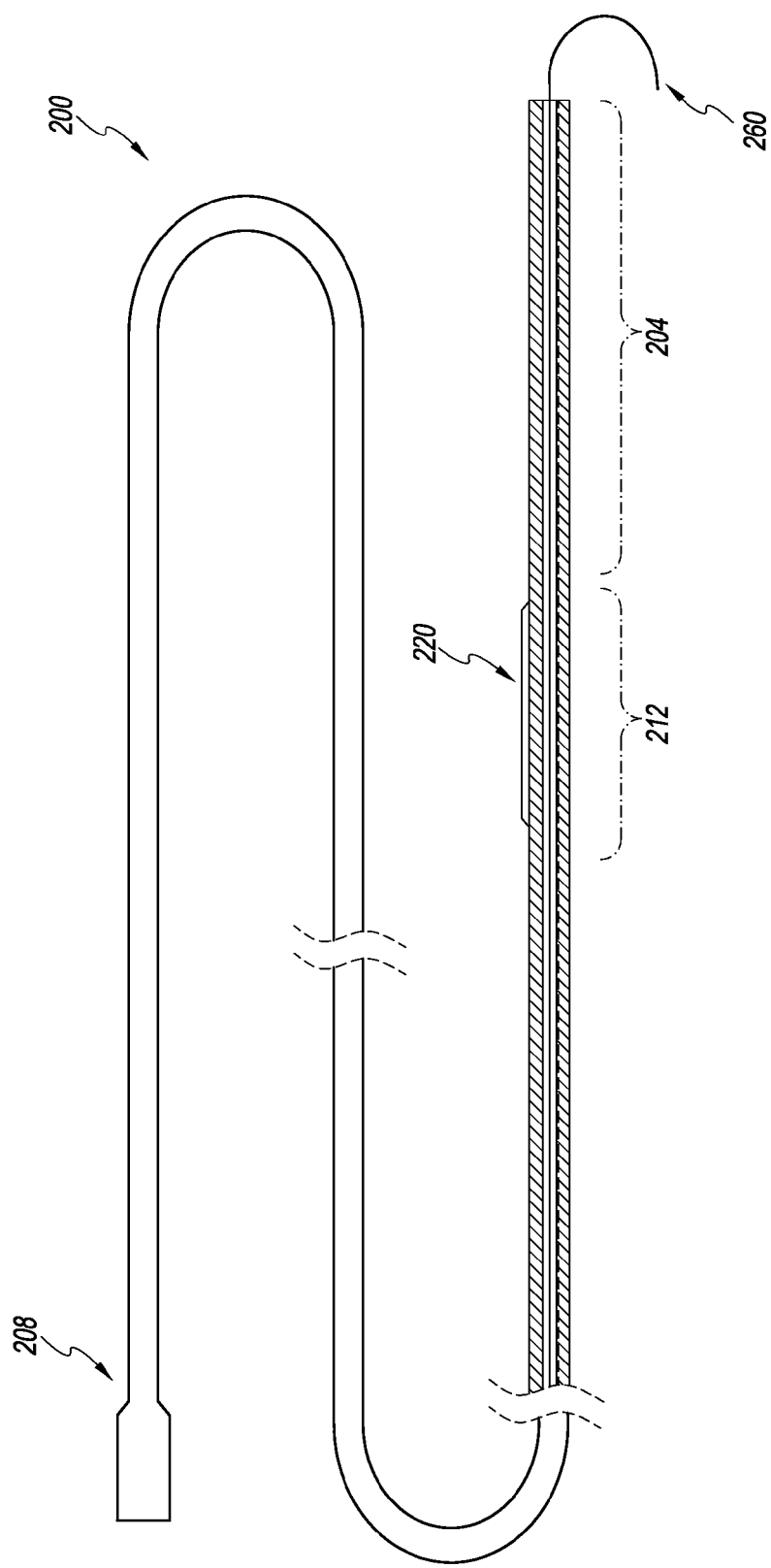
FIG. 3D is a plan view of a heart valve procedure catheter for preparing a valve portion, e.g., a leaflet, prior to placement of an implant in which the distal section is in cross-section and is drawn to a larger scale than the proximal section to emphasize certain details.

If it is desired to deliver the piercing member 124 over the wire 128, the elongate body 124A can be made hollow as in FIG. 3A. If it is desired to minimize the profile of the piercing member 124, the elongate body 124A can be made solid as in FIG. 3B.

The piercing member 124 and elongate body 124A scan take any suitable shape, but preferably are sufficiently stiff and/or sharp to advance through the myocardium to create a trasnapical channel TAC through the heart wall. The TAC extends from an internal opening in the internal apical portion of a ventricle to an external opening at an outside heart wall. The TAC is preferably very small but large enough to permit a blocking member (e.g., balloon) to be advanced from inside the LV to the outside of the LV in the pericardial space.

The delivery platform 108 is configured to be advanced from the catheter body 104 along the piercing member 124. The delivery platform 108 preferably includes a thin walled tubular body 140 that includes a distal port 144 and a blocking member 148 disposed just proximal to the distal port 144. The blocking member 148 can be any device that is able to expand in the pericardial space, as discussed below, to a transverse width that is sufficient to block the external opening of the TAC. FIG. 3B illustrates an inflation lumen 150 disposed in the thin walled tubular body for inflating a balloon. FIG. 6 shows the distal portion of the blocking member 148 emerging from the external opening in the pericardial space.

The blocking member 148 can be a device that expands without requiring an inflation medium to be delivered for expansion. For example, the member 148 can have a low profile state for delivery and an enlarged state after it is placed in the pericardial space. Nitinol or other shape memory material can be used. The shape memory material can be in several different configurations. In one configuration, the shape member is a stress-induced shape memory. A blocking member 148 formed of stress-induced shape memory material can be delivered in a compressed state if it is constrained from expansion in some manner, e.g., by an outer sheath. Retraction of the sheath can enable this sort of blocking member 148 to expand in the pericardial space by releasing the strain energy that is stored in the shape memory material. The sheath could be analogous to the sheath 170 discussed below.

In one technique, after the piercing member 124 is advanced through the myocardium to create the TAC, the tubular body 140 is advanced through the TAC. Such advancement can be along the elongate body 124A proximal of the piercing member 124. The piercing member 124 can be withdrawn from the pericardial space back into the catheter body 104 in some embodiments. In other embodiments, the thin walled tubular body 140 can be configured (e.g., with sufficient column strength and/or a tapered profile) to be advanced unguided through the TAC. Unguided advancement of the tubular body 140 enables the piercing member 124 to be withdrawn from the pericardial space, e.g., removed from the patient's body, to minimize the time that the piercing member is in the pericardial space. In other embodiments, a separate guide member is exchanged for the piercing member and the guide member is used to advance the tubular body 140.

In one embodiment, the tubular body 140 extends proximally from the apex of the left ventricle across the mitral valve space and into a distal port, e.g., the port 132, of the catheter body 104. The tubular body 140 is configured such that when the blocking member 148 is deployed the tubular body 140 can be placed in tension. When in tension or taut, the tubular body 140 provides a predictable platform for advancing other devices into the mitral valve space.

Figure 7:
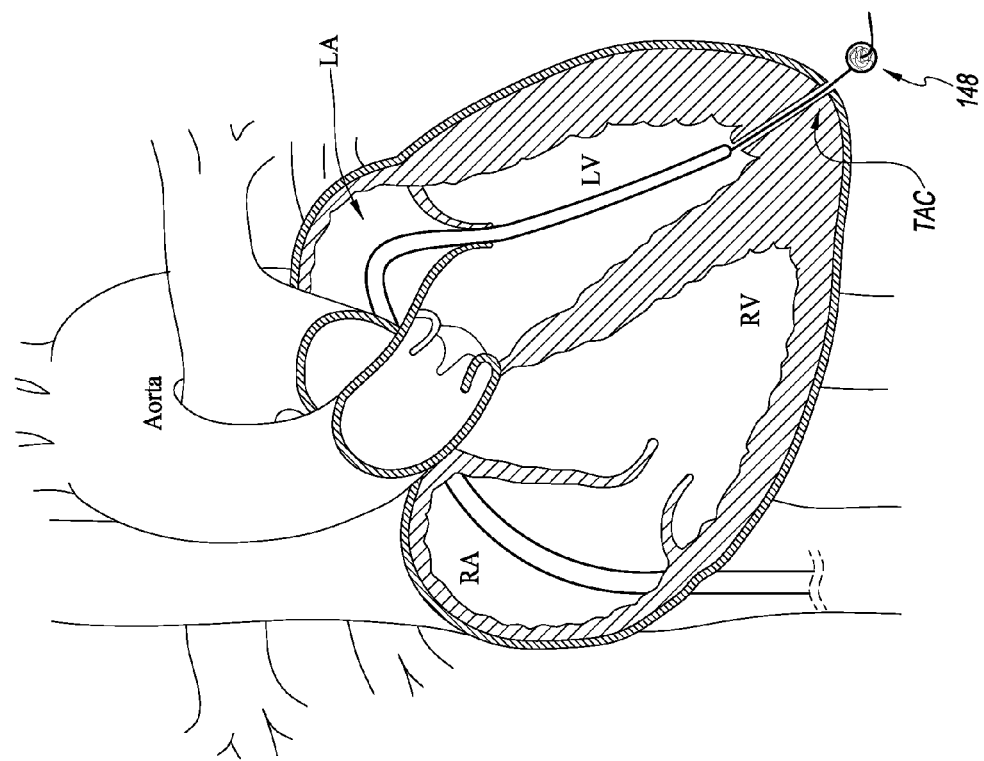
Figure 8:
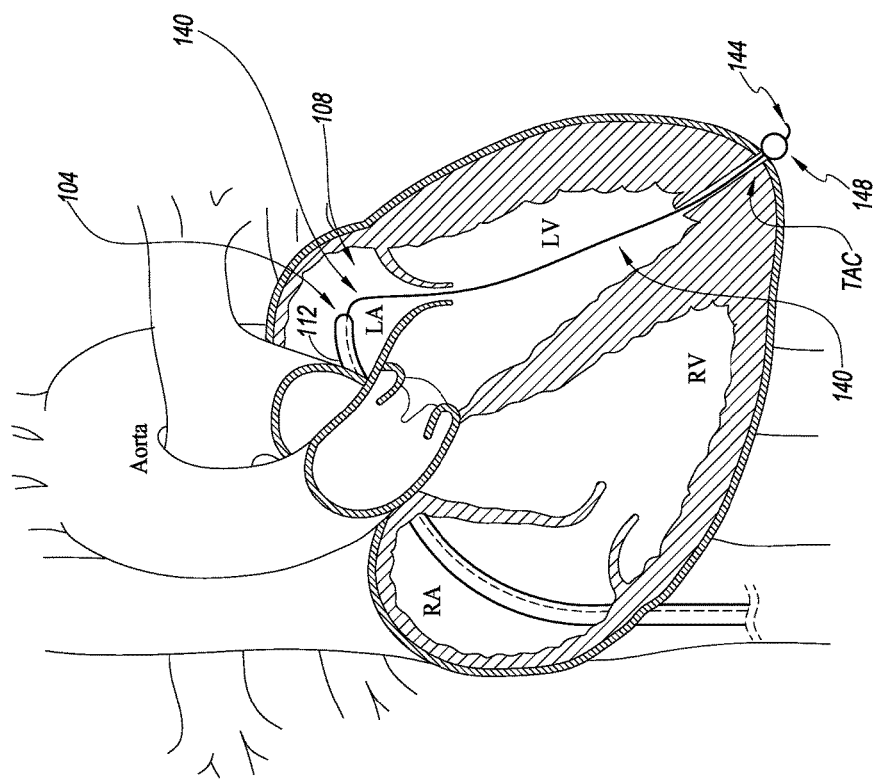
Figure 9:
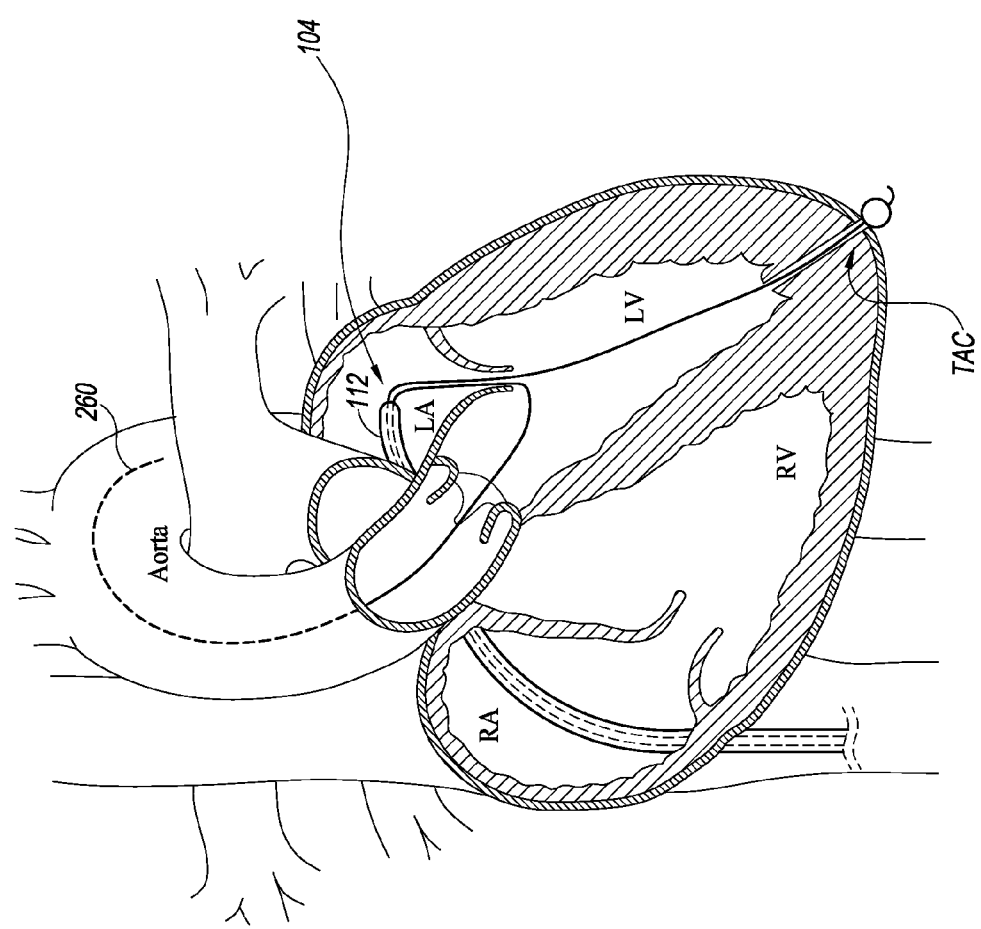

FIGS. 7 and 8 illustrate a simple way of tensioning the delivery platform 108. FIG. 7 shows that the blocking member 148 can be actuated from a low profile state for advancement through the TAC to an enlarged state for blocking the TAC to prevent bleeding into the pericardial space. Once the blocking member 148 is in the enlarged state, the distal portion 112 of the catheter body 104 can be withdrawn from a position in the LV to a position in the LA above the mitral valve. This movement reduces the slack in the tubular body 140 and eventually begins to tension the tubular body 140.

The catheter body 104 is configured with sufficient stiffness to provide resistance to bending such that withdrawing the catheter body from the position in FIG. 7 to the position in FIG. 8 provides sufficient tension on the tubular body 140 for delivery of valve prostheses as discussed below. In particular, a braided structure B can be placed in the wall of the catheter body 104 that makes at least the distal portion 112 resistant to bending in this and other maneuvers intended to tension the body 140.

A heart valve implant catheter 160 can be advanced over the tubular body 140 after the tubular body 140 is tensioned. The implant catheter 160 can be advanced within a lumen formed in the catheter body 104. In one embodiment, the implant catheter 160 has a registration portion 164 disposed at a distal end thereof. The registration portion 164 can include a length of the implant catheter 160 disposed distal of an implant zone 168 having an implant I thereon. The implant zone 168 can vary from implant to implant, but for a replacement mitral valve, the implant zone 168 can include at least a distal portion in which a ventricular side of a replacement mitral valve is disposed and a proximal portion in which an atrial side of a replacement mitral valve is disposed. A central portion is disposed between the distal and proximal portions. The proximal and distal portions are configured to be disposed over proximal and distal portions of the delivery platform 112. The registration portion 164 can have a length that is approximately equal to the distance from the mitral valve annulus to a registration surface, e.g., ventricular tissue disposed around the internal opening of the TAC.

In one technique, the heart valve implant catheter 160 is advanced over the tubular body 140 into the left atrium. The catheter 160 is further advanced into the left ventricle. Further advancement causes the registration portion 164 of the heart valve implant catheter to contact the left ventricle at the internal opening into the TAC. Such contact can be ascertained by any suitable means, such as by reference to echocardiography or other visualization or by tactile feel. By providing the registration portion 164, the procedure time required for positioning the mitral valve at the correct superior-inferior position can be reduced or minimized.

In one approach, the registration portion 164 is sized or can be selected from a range of catheter having differently sized registration portions 164 to fit the particular patient. For example, echocardiography can be used to ascertain the distance from the plane of the valve annulus to the LV apex. This distance can be used to size or select the appropriate catheter with the appropriately sized registration portion 164. The delivery platform 108 can be deployed as in FIG. 2 and thereafter an echocardiographic analysis can be done of the heart and the platform 108. This analysis can tell the clinician how long the registration portion 164 should be.

Figure 10:
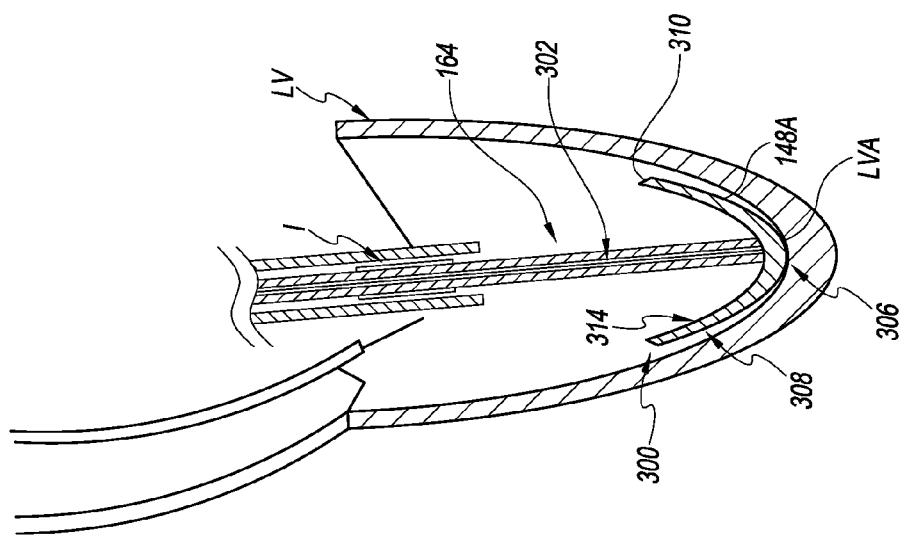
FIG. 10 illustrates a first embodiment of a system that can be implemented without a transapical channel.

The interaction of the registration portion 164 is also illustrated and described below in connection with the embodiment of FIG. 10. A difference among the embodiments of FIGS. 2-9 and 11 and the embodiment of FIG. 10 is the absence or presence of a portion of a delivery system in the internal left ventricle apex. In FIG. 10 a portion of the system provides a convex registration member or surface. As a result the registration portion 164 contacts this registration member or surface of the system rather than the internal heart wall. In the other embodiments, the registration portion 164 may directly contact the internal surface of the left ventricle at least momentarily during placement of the implant I, as discussed herein.

In other embodiments, the registration portion 164 can be eliminated. For example, standard visualization techniques can be used to locate radiopaque markers or the implant itself to confirm superior-inferior position.

In addition to superior-inferior position, some implant benefit from proper orientation relative to the plane of the valve annulus. The mitral valve annulus can be approximated by a plane that extends through the inferior-superior mid-point of the zone of attachment of the leaflet to the heart wall of a portion or all aspects of the leaflets. Obtaining the correct attitude of a mitral valve implant I relative to this plane can be accomplished by orienting the tubular body 140 perpendicular to this plane. The tubular body 140 can be so oriented by adjusting the anterior-posterior position of the distal port 132 of the catheter body 104 after the blocking member 148 has been expanded.

FIG. 3A-1 shows another embodiment of the catheter body 104 in which small adjustments of the orientation of the tubular body 140 can be provided. A steering system can include a plurality of, e.g., four steerable members St as shown. Each of these members can extend between the proximal and distal end of the catheter body 104. Actuating these members can enable the trajectory of the delivery platform 108 out of the catheter body 104 to be fine adjusted. Orientation of the platform 108 can be confirmed by echocardiography.

While the steering system of FIG. 3A-1 is not required in view of the trajectory defined by the position of the port 132 and the location of the LV apex, it can be provided for fine adjustments for some patients with unique anatomy. In preferred techniques, the delivery platform extends along an axis Ad is within about 45 degrees of an axis Ap perpendicular to the plane of P the annulus A. That is the angle α between the axes Ap and Ad is within about 45 degrees as shown in FIG. 8A. In other preferred techniques, the delivery platform is within about 20 degrees of perpendicular to the plane of the annulus. In other preferred techniques, the delivery platform is within about 10 degrees of perpendicular to the plane of the annulus.

The manner of placing the implant I can vary. In some embodiments, the implant I includes a self-expanding structure, such as a stent body. Such a device may be deployed by retracting a sheath 170 having a distal portion 170A disposed over the implant I prior to deployment. If the registration portion 164 is present, an assembly including the heart valve implant catheter 160 and the sheath 170 are advanced over the delivery platform 112 until the registration portion 164 abuts the heart wall at the LV apex (or a registration member or structure as discussed elsewhere herein). Thereafter, the heart valve implant catheter 160 can be held in position while the sheath 170 is withdrawn. This allows for initial deployment of a distal portion of the implant I. If the positioning is correct, the sheath 170 can be further withdrawn to release a proximal portion of the implant I.

In other embodiments, the heart valve implant catheter 160 is used to expand a support structure of the implant I by applying outward pressure, such as by inflating a balloon upon which the implant I is disposed. In such an embodiment, the sheath 170 can be eliminated or it can remain in place in order to protect the implant I during advancement through the vasculature and/or over the delivery platform 112. The catheter 160 can be modified to have an inflation lumen in fluid communication with a balloon upon which the implant I can be disposed.

In further variations, it is desired to eliminate the TAC. One approach enables the registration portion 164 to provide a stable trajectory between the distal port 132 of the catheter 104 through the mitral valve annulus. This trajectory will be substantially perpendicular to the plane of the annulus or at least within a close range of angles from perpendicular as discussed below. In one approach illustrated in FIG. 10, a guide member 300 similar to the delivery platform 108 is provided. The guide member 300 includes an elongate body 302 body (e.g., a solid or tubular body) for tracking the implant catheter 160 over. The guide member 300 has an expandable member 148A disposed at the distal end. The guide member 300 and expandable member 148A need not be configured to be in tension. Instead, the expandable member 148A is configured to be received in the LV apex and provide a landing zone or surface for the registration portion 164. The registration portion 164 can be stiffened so that it can be placed in compression. The compression can be caused by distal urging of the proximal end of the implant catheter 160, which is resisted by the heart wall via the expandable member 148A.

The expandable member 148A provides some cushioning for the heart wall and preferably also is formed as an inverted cone or angled surface that directs the distal end of the registration portion 164 to the correct position and/or orientation. In one implementation, the expandable member 148A includes a rounded distal tip 306 that is shaped to generally conform to the inside of the left ventricle apex LVA. A distal face 308 of the expandable member 148A is rounded in a way that generally conforms to average shape of the ventricle. The distal face 308 extends from the rounded tip toward a proximal periphery 310. A proximal face 314 of the expandable member 148A is curved inwardly to provide a concave structure or surface. The concave structure of the proximal face 314 preferably has its distal-most portion disposed at the tubular body of the guide member 300. In this way, the implant catheter 160 can be guided to the corrected position and/or orientation beneath the mitral valve. In particular, the implant catheter 160 can be advanced over the body 302 into the concave structure of the expandable member 148A, into close adjacency with the left ventricle apex LVA. The trajectory of the catheter 160 from the distal port 132 to the positioned defined by the concave structure of the expandable member 148A is closely perpendicular to the plane of the mitral valve annulus (or can be adjusted to be so using the steering system discussed above).

In a further variation, the guide member 300 is eliminated and the implant catheter 160 is delivered from the distal port 132 of the catheter 104 into direct contact with the LVA.

Figure 11:
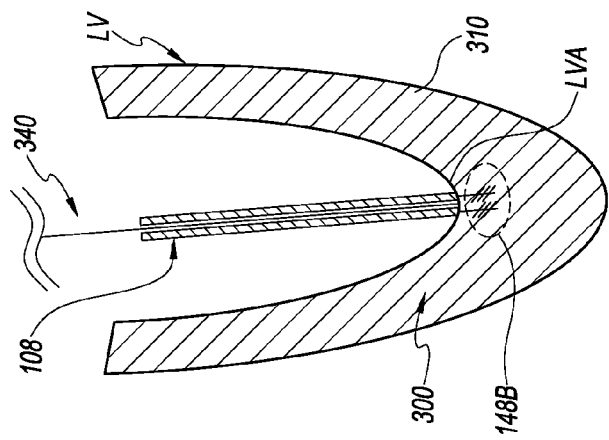
FIG. 11 illustrates a second embodiment of a system that can be implemented without a transapical channel.

Further variants can be provided in which the delivery platform 108 is tensioned but without requiring the TAC to be formed through heart wall. For example, FIG. 11 illustrates a plurality of tines 148B disposed in the wall adjacent to the LVA. The tines 148B could be expandable, but are not required to be. In some embodiments, the tines 148B are extended from the delivery platform 108. Preferably the tines 148B have a working length at their distal ends that is not greater than one-quarter the average wall thickness of the heart at the LVA. In some embodiments, the tines have a working length at their distal ends that is less than about 1 mm, to minimize the chance of the tines extending all the way through the heart wall. In the illustrated embodiment, the delivery platform 108 with tines 148B is delivered over a previously placed wire 340. The wire 340 can have a sharp tip to enable it to be temporarily lodged in the wall of the ventricle or could be soft like the atraumatic tip guidewire 128. Once the tines 148B are secured in the ventricle wall, the delivery platform can be tensioned to control the delivery path of the implant catheter 160.

After the procedure is complete, the tines 148B can be actuated to a removal configuration such that the delivery platform 108 can be withdrawn. In one embodiment, the tines 148B are initially tilted to a position transverse to the longitudinal axis of the delivery platform. The tines 148B engage the wall tissue around the ventricle when the delivery platform 108 is pulled back (e.g., tensioned). In some embodiments, when the delivery platform 108 is in compression the tines 148B disengage from the hear wall. For example, if the tines can be urged a little deeper into the wall of the ventricle the tilt back into alignment with the longitudinal axis of the delivery platform 108 and can be withdrawn proximally from the ventricle wall.

In other embodiments, the tines 148B could be configured to be separated from the rest of the delivery platform 108 so that the tines are left in place but the rest of the delivery platform 108 is easily removed. Various techniques facilitate removal of the delivery platform 108 including torqueing the proximal length of the delivery platform 108 to unscrew a joint adjacent to the tines 148B.

For some patients and for some implants, it is advantageous to prepare at least one of the leaflets prior to placement of the valve. For example, the anterior mitral valve leaflet is flexible but tough. So, its presence between the implant valve and the heart wall from which the leaflet(s) extend can cause a resisting force to the valve structures that are placed over the anterior and/or posterior leaflet. While the mounting structures of the prosthetic valve can be stiffened to overcome the force of the anterior leaflet (and other parts of the natural mitral valve), it may be preferable to mount a less rigid replacement valve in the heart. Heart enlargement is one side effect of congestive heart disease that can reduce valvular sufficiency. Placing overly rigid structures in the rapidly moving heart could add to swelling of the heart or heart damage. For these reasons it would be better to minimize the force applying capability at least of the anterior leaflet.

To this end, the delivery system 100 can include a heart valve procedure catheter 200 independently advanceable from the tubular catheter body 104. The heart valve procedure catheter 200 can be adapted to be positioned for procedures prior to placement of heart valve implant. The procedure catheter 200 can include a distal anchoring zone 204, a proximal advancement and manipulation zone 208 and a procedure zone 212 disposed between the manipulation zone 208 and the anchor zone 204. The procedure zone 212 can have any useful implements to prepare the anterior leaflet and/or can be configured to directly prepare the anterior leaflet.

In one arrangement, the procedure zone 212 has a cutting device 216 disposed thereon that can be brought into contact with the anterior leaflet to segment the leaflet. The cutting device 216 can be one or a plurality of ridges 220 disposed along the length of the procedure zone 212. The procedure catheter 200 can be arranged as discussed in U.S. Pat. No. 8,172,856 to facilitate positioning of the procedure zone 212 along the mitral valve. In some embodiments, the anchor zone 204 provides a fulcrum about which to pivot the procedure zone 212. The pivoting of the procedure zone 212 facilitates placement of the procedure zone along a specific portion of the anterior leaflet. For example, the procedure zone 212 can be placed along a central third of the leaflet by pivoting the manipulation zone 208. A central third of the anterior leaflet is measured as a zone extending one-third of the length of anterior leaflet adjacent to the free edge of the leaflet, where the absolute center of the anterior leaflet at the free edge is within or at the end of the range. Pivoting the manipulation zone 208 can be provided to rotating the proximal end of the procedure catheter 200 about a central axis of the proximal end. In other embodiments, the procedure zone 212 is placed along a central quartile of the anterior leaflet. In some embodiments, the procedure zone 212 is placed within a central half of the anterior leaflet. A central half of the anterior leaflet is measured as fifty percent of the length of anterior leaflet adjacent to the free edge of the leaflet, where the absolute center of the anterior leaflet at the free edge is within or at the end of the range.

While some heart valve placement benefits from segmenting the anterior leaflet or another portion of the mitral valve, some valves can be advantageously placed with the aid of a mere retraction of the leaflet. In one embodiment, the procedure zone 212 is configured to retract the anterior leaflet. For example, the procedure zone 212 of the procedure catheter 200 can be stiffened to prevent the zone 212 from buckling when brought into contact with a portion of the leaflet. The portion contacted can be a central half, one-third or quartile of the leaflet as discussed above. In these embodiments, the procedure zone 212 need not include the ridges 220 for cutting the leaflet, but instead can just include a surface adapted to displace the free edge of the leaflet.

In one variation a retraction portion if provide on one portion of the procedure zone 212 and the ridge 220 or other segmenting portion is provided on another portion of the procedure zone. In these embodiments, the procedure catheter 200 is preferably advanced in an orientation in which the portion desired to interact with the anterior leaflet is on the inside cure of the catheter body when placed. In this context, the inside curve includes the concave or bight forming portion of the procedure zone 212. If the preference is to merely retract, the retraction zone can be positioned on the inside curve and the ridges 220 on the outsides curve (the convex side). If the preference is to merely retract, the ridges are positioned on the inside curve and the retraction zone on the outsides curve.

Placement of the procedure catheter 200 can be achieved by advancing a guide member 260 (e.g., a guidewire) out of a distal port of the catheter body 104. The guide member 260 is delivered through a notch formed between medial and lateral chordae that actuated the anterior leaflet of the mitral valve. The guide wire 260 extends from the notch through the LV outflow tract and the AV into the aorta. Contacting with the anatomy distal the notch (e.g., a wall of the ascending aorta) and the notch causes the retraction zone or the ridges 220 of the procedure catheter 200 to be in a central zone. The central zone can be an anatomical portion the produces bisection of the anterior leaflet or other approximately equal segmentation.

The procedure catheter 200 is positionable based on the anchoring function of the anchor zone 204 and/or the notch between the medial and lateral chordae and in response to torqueing the manipulation zone 208 which can include a proximal portion of the procedure catheter 200 outside the patient. Further details of structures can be used in the procedure catheter 200, such as to position the catheter in a quick yet precise manner are found in U.S. Pat. No. 8,172,856, which is incorporated by reference herein.

Although the present invention has been disclosed with reference to certain specific embodiments of devices and methods, the inventors contemplate that the invention more broadly relates to methods disclosed above, such as those useful for orienting a catheter with respect to an anatomical structure, as well as performing diagnostic and/or therapeutic procedures in the heart or adjacent the heart. Accordingly, the present invention is not intended to be limited to the specific structures and steps disclosed herein, but rather by the full scope of the attached claims.

What is claimed is:

1. A delivery system for rapid placement of heart implants at a mitral valve, comprising:
    a tubular catheter body being sufficiently long and flexible to be advanced from a peripheral blood vessel access site to an atrium of the heart;
    a piercing member configured to be advanced from the tubular catheter body to create a transapical channel from an internal apical portion of a ventricle to an outside heart wall;
    a delivery platform configured to be advanced from the tubular catheter body, the delivery platform comprising an elongate tension member and an enlargeable member disposed on a distal portion of the elongate tension member, the enlargeable member configured to be enlarged in a pericardial space of an intact chest wall to cover an area of the outside heart wall surrounding an opening of the transapical channel, wherein a portion of the elongate tension member is configured to extend proximally from the distal portion and to span the transapical channel when the enlargeable member is enlarged in the pericardial space; and
    a heart valve implant catheter;
    wherein at least a heart valve implant mounted on the heart valve implant catheter is separable from the delivery system such that the heart valve implant catheter, the elongate tension member, the piercing member, and the enlargeable member can be removed while leaving the heart valve implant in place.

2. The delivery system of claim 1, further comprising a heart valve procedure catheter independently advanceable from the tubular catheter body, the heart valve procedure catheter adapted to be positioned for procedures prior to placement of heart valve implant.

3. The delivery system of claim 2, wherein the heart valve procedure catheter comprises a retraction zone adapted to displace the anterior leaflet anteriorly against a heart wall.

4. The delivery system of claim 2, wherein the heart valve procedure catheter comprises a resection device configured to perform at least one incision on the anterior leaflet.

5. The delivery system of claim 4, wherein the heart valve procedure catheter is configured to bisect the anterior leaflet at a central zone of the leaflet.

6. The delivery system of claim 1, wherein the enlargeable member comprises an inflatable balloon.

7. A delivery system for rapid placement of heart implants at a mitral valve, comprising:
a tubular catheter body being sufficiently long and flexible to be advanced from a peripheral blood vessel access site to an atrium of the heart;
a delivery platform configured to be advanced from the tubular catheter body, the delivery platform comprising an elongate tension member and an enlargeable member disposed on a distal portion of the elongate tension member, the enlargeable member configured to be enlarged adjacent to the apex of the left ventricle to cover an area of the heart wall at the apex; and
a heart valve implant catheter having an implant zone and a registration portion extending distally from the implant zone, the implant zone configured to secure an implant mounted thereon in a first configuration in which the implant is longitudinally fixed relative to the heart valve implant catheter, the implant configured to move from the implant zone to a second configuration in which the heart valve implant catheter is longitudinally movable relative to the implant, thereby allowing the delivery system to be withdrawn from the heart while leaving the implant in the heart, the registration portion being configured to position the implant at the proper distance from the left ventricle apex.

8. The delivery system of claim 7, further comprising a heart valve procedure catheter independently advanceable from the tubular catheter body, the heart valve procedure catheter adapted to be positioned for procedures prior to placement of heart valve implant.

9. The delivery system of claim 8, wherein the heart valve procedure catheter comprises a retraction zone adapted to displace the anterior leaflet anteriorly against a heart wall.

10. The delivery system of claim 8, wherein the heart valve procedure catheter comprises a resection device configured to perform at least one incision on the anterior leaflet.

11. The delivery system of claim 8, further comprising a guidewire for advancement through the tubular catheter body across the aortic valve and into the descending aorta, the heart valve procedure catheter adapted to be advanced over the guidewire to be disposed along a path from the ascending aorta through the aortic and mitral valves and across the intra-atrial septum.

12. The delivery system of claim 7, wherein the enlargeable member comprises an inflatable balloon.

13. The delivery system of claim 7, wherein the tubular catheter body includes a steering system for adjusting a trajectory between a distal port of the tubular catheter body and the left ventricle apex.

14. A delivery system for rapid placement of heart implants at a mitral valve, comprising:
a tubular catheter body being sufficiently long and flexible to be advanced from a peripheral blood vessel access site to an atrium of the heart, the tubular catheter body comprising a distal port and a steering system for adjusting a positioning of the distal port;
a delivery platform configured to be advanced from the distal port of the tubular catheter body, the delivery platform comprising an elongate tension member and a heart wall interface disposed on a distal portion of the elongate tension member, the heart wall interface configured to engage tissue on an inside surface of the heart adjacent the apex of the left ventricle to counteract a tension applied to the elongate tension member, the distal portion of the elongate tension member configured to be substantially fixed relative to the tissue adjacent the apex of the left ventricle when the heart wall interface engages said tissue, a proximal portion of the elongate tension member extending proximally of the distal portion being pivotable about the heart wall interface by adjusting the positioning of the distal port;
wherein the delivery platform provides rapid and accurate orientation of a heart valve implant catheter delivered over the elongate tension member.

15. The delivery system of claim 14, wherein the heart wall interface comprises an enlargeable member configured to conform to the inside wall of the ventricle over the apex.

16. The delivery system of claim 15, wherein the enlargeable member is a concave structure configured to receive the elongate tension member of the delivery platform to guide the distal end thereof to an orientation enabling the elongate tension member to be closely proximate to perpendicular to a plane of a valve annulus of a patient being treated with the system.

17. The delivery system of claim 14, wherein the heart wall interface comprises at least one tine disposed on a distal end of the delivery platform.

18. The delivery system of claim 17, wherein the tine is actuatable from a low profile state to a heart wall tissue engaging state.

19. The delivery system of claim 18, wherein the tine is actuatable from the heart wall tissue engaging state to a removal state.

20. The delivery system of claim 17, wherein at least the tine of the heart wall interface is separable from the elongate tension member of the delivery platform.

* * * * *